United States Patent
Donlon et al.

(10) Patent No.: US 9,907,921 B2
(45) Date of Patent: *Mar. 6, 2018

(54) TRACHEOSTOMY TUBE WITH INNER CANNULA

(71) Applicant: Covidien LP, Mansfield, MA (US)

(72) Inventors: Kieran Donlon, Co. Longford (IE); Declan Kiernan, Co. Longford (IE); Kamlesh Sethiya, Co. Westmeath (IE); Emmet Bolger, Athlone (IE); Alan Finneran, Co. Offaly (IE); James Curley, Athlone (IE)

(73) Assignee: Covidien LP, Mansfield, MA (US)

( * ) Notice: Subject to any disclaimer, the term of this patent is extended or adjusted under 35 U.S.C. 154(b) by 554 days.

This patent is subject to a terminal disclaimer.

(21) Appl. No.: 14/538,577

(22) Filed: Nov. 11, 2014

(65) Prior Publication Data

US 2015/0136123 A1 May 21, 2015

Related U.S. Application Data

(60) Provisional application No. 61/904,319, filed on Nov. 14, 2013.

(51) Int. Cl.

| A61M 16/04 | (2006.01) |
| A61M 16/08 | (2006.01) |
| A61M 16/00 | (2006.01) |
| A61M 16/10 | (2006.01) |
| A61M 16/16 | (2006.01) |

(52) U.S. Cl.
CPC .... *A61M 16/0497* (2013.01); *A61M 16/0434* (2013.01); *A61M 16/0465* (2013.01); *A61M 16/0816* (2013.01); *A61M 16/009* (2013.01); *A61M 16/0463* (2013.01); *A61M 16/0475* (2014.02); *A61M 16/1045* (2013.01); *A61M 16/16* (2013.01); *A61M 2230/435* (2013.01)

(58) Field of Classification Search
CPC .......... A61M 16/0434; A61M 16/0463; A61M 16/0465; A61M 16/0475; A61M 16/0481; A61M 16/0497; A61M 16/0816
See application file for complete search history.

(56) References Cited

U.S. PATENT DOCUMENTS

| 3,169,529 A | 2/1965 | Koenig |
| 3,225,767 A | 12/1965 | Smith |
| 4,817,598 A | 4/1989 | LaBombard |
| 5,386,826 A | 2/1995 | Inglis et al. |
| 5,864,938 A | 2/1999 | Gansel et al. |

(Continued)

OTHER PUBLICATIONS

Tracoe Twist ref 304, Fenestrated Tracheostomy Tube, sales@bryanmedical.net; http://www.bryanmedical.net/Tracoe/Tracoe_Twist_304.html.

(Continued)

*Primary Examiner* — Lynne Anderson

(57) ABSTRACT

A tracheal tube assembly includes an outer cannula configured to be positioned in a patient airway and an inner cannula configured to be disposed inside the outer cannula. The tracheal tube assembly further includes a flange member secured about the outer cannula, and an outer cannula connector coupled to a proximal end of the outer cannula. The inner cannula includes a proximal end region with features that facilitate insertion and/or removal.

19 Claims, 18 Drawing Sheets

(56) References Cited

U.S. PATENT DOCUMENTS

| | | | |
|---|---|---|---|
| 6,019,753 | A | 2/2000 | Pagan |
| 6,024,730 | A | 2/2000 | Pagan |
| 6,135,110 | A | 10/2000 | Roy |
| 6,248,099 | B1 | 6/2001 | Bell |
| 6,679,871 | B2 | 1/2004 | Hahnen |
| 9,010,326 | B2 * | 4/2015 | Bruggeman ...... A61M 16/0465 128/204.17 |
| 2004/0068278 | A1 | 4/2004 | Fleischman et al. |
| 2007/0012317 | A1 | 1/2007 | Flagler et al. |
| 2007/0255258 | A1 | 11/2007 | Matlock et al. |
| 2008/0149108 | A1 | 6/2008 | Neame |
| 2010/0244432 | A1 | 9/2010 | Neame et al. |
| 2011/0083672 | A1 | 4/2011 | Webster et al. |

OTHER PUBLICATIONS 204A extra-long speaking tube, type B; http://www.kapitex.com/tracheostomy/tracoecomfort/tracoecomfort-204a/.

SIMS Portex Inc., "Tracheostomy Care Handbook, A Guide for the Health Care Provider", (1998).

Portex—UniPerc adjustable flange tracheostomy tubes, Smiths medical.

* cited by examiner

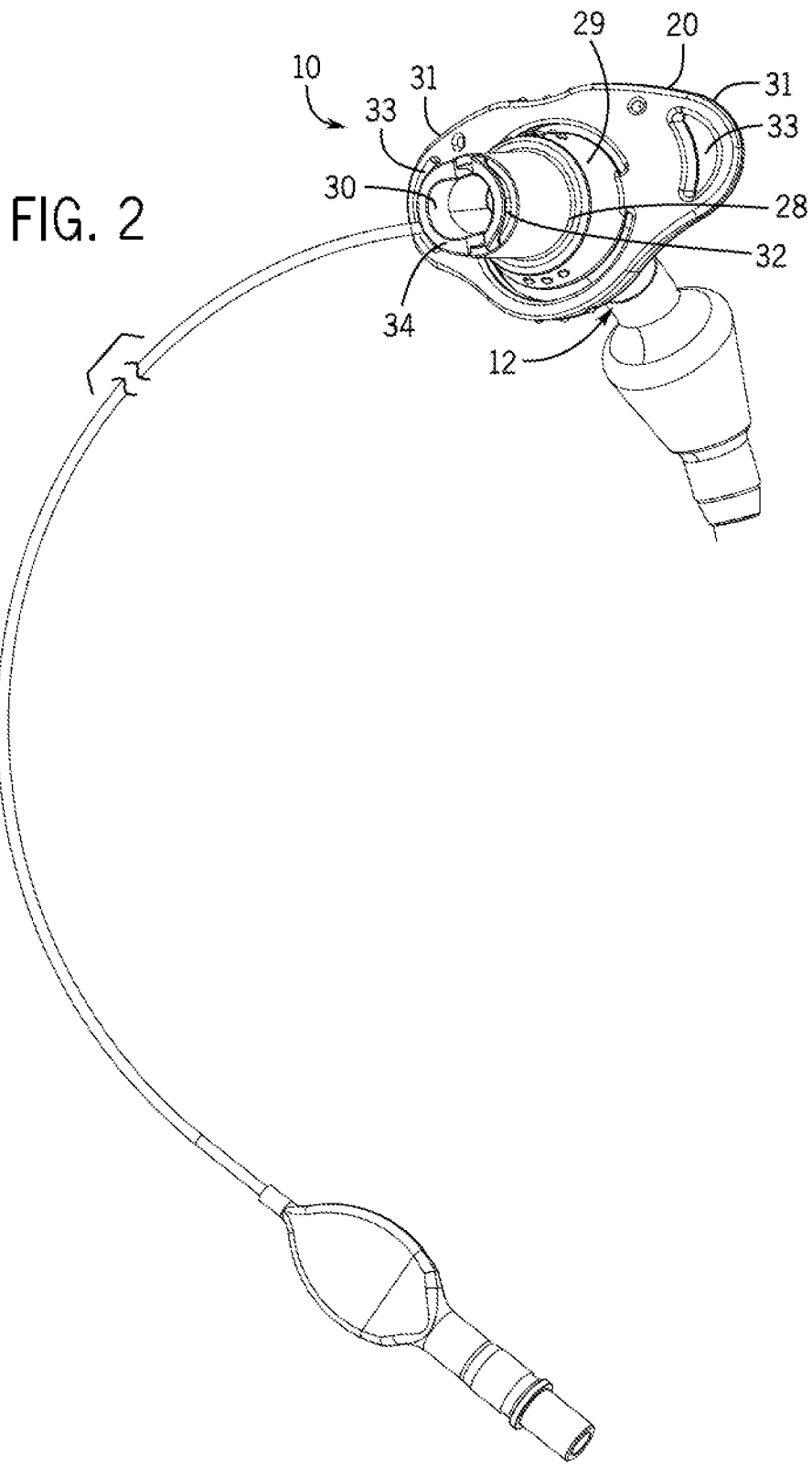

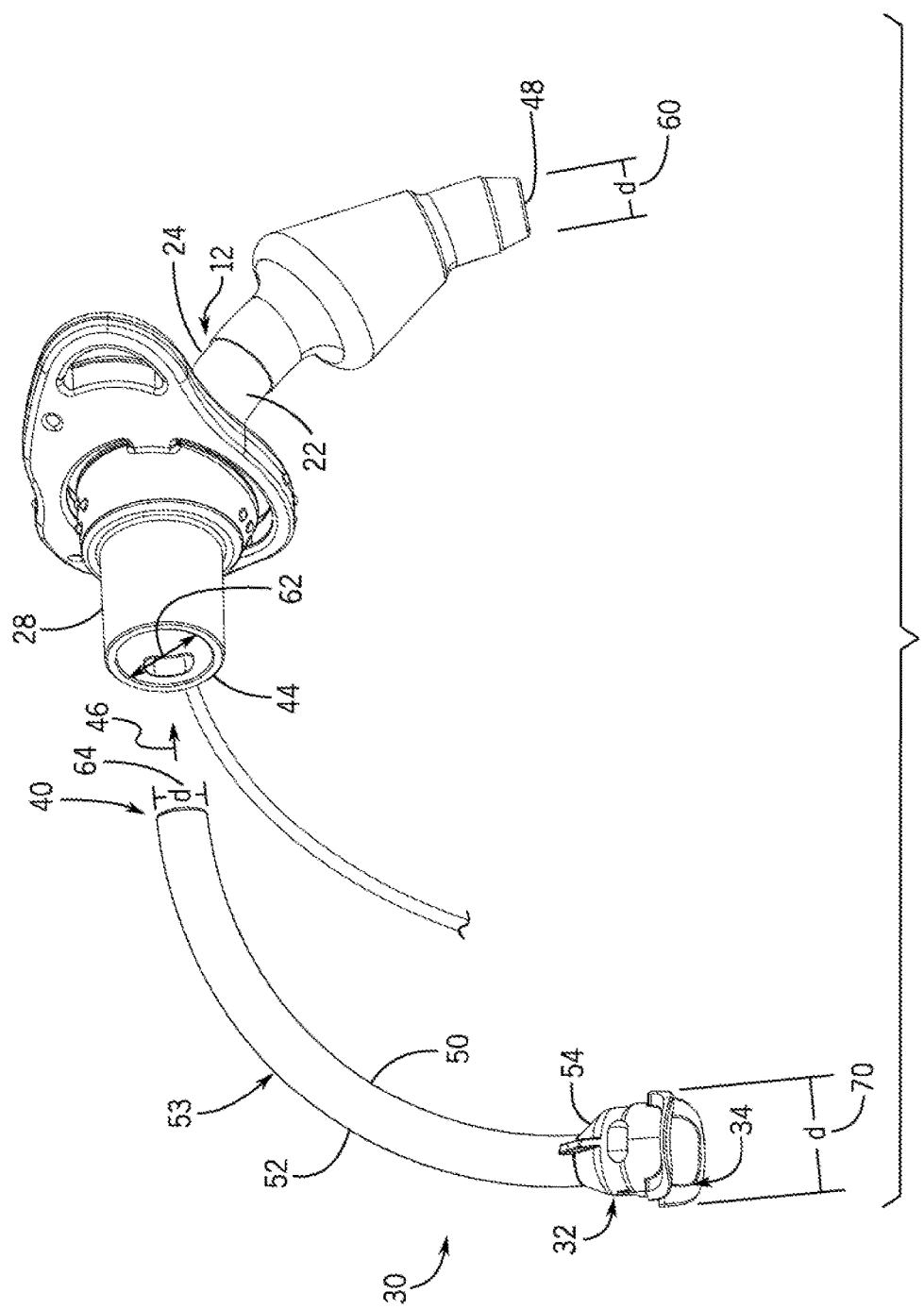

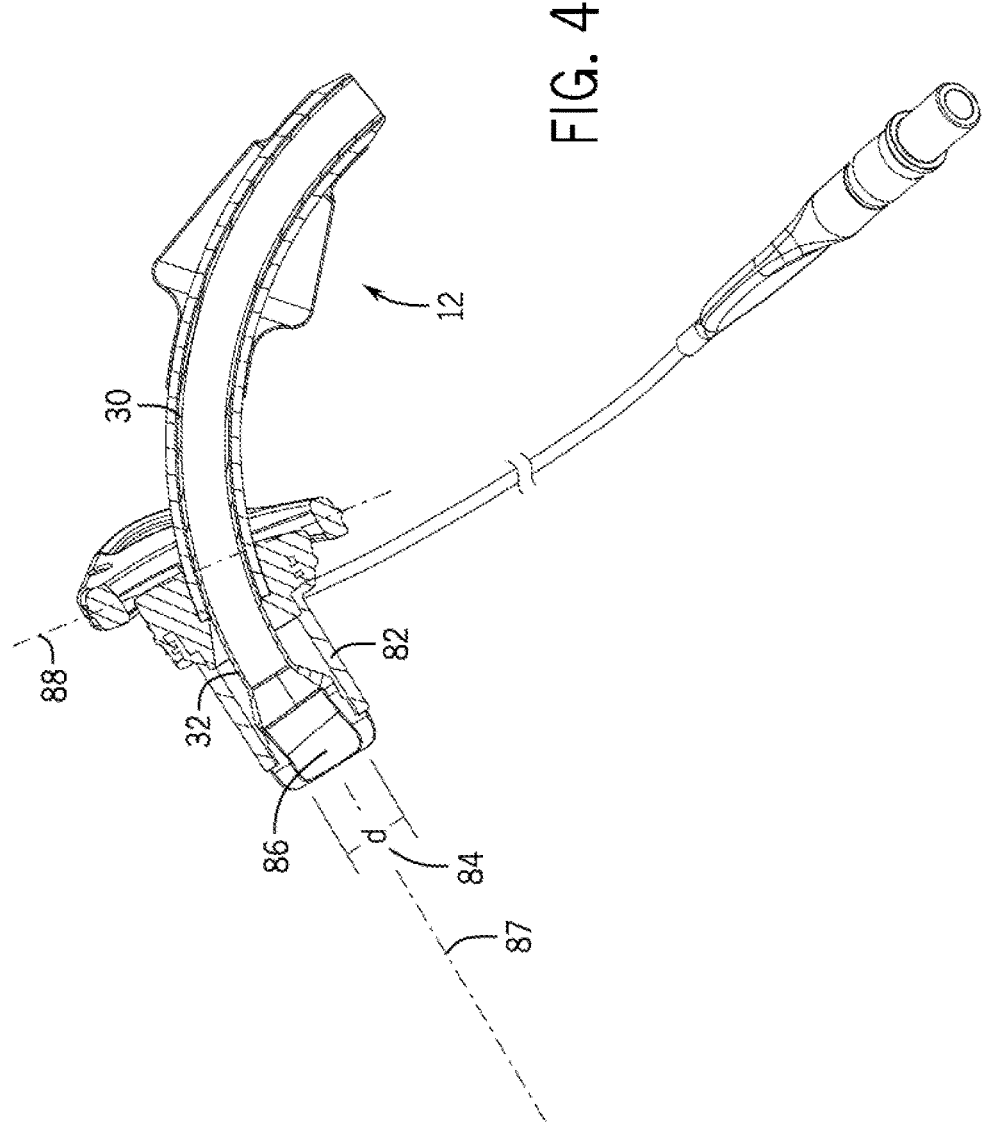

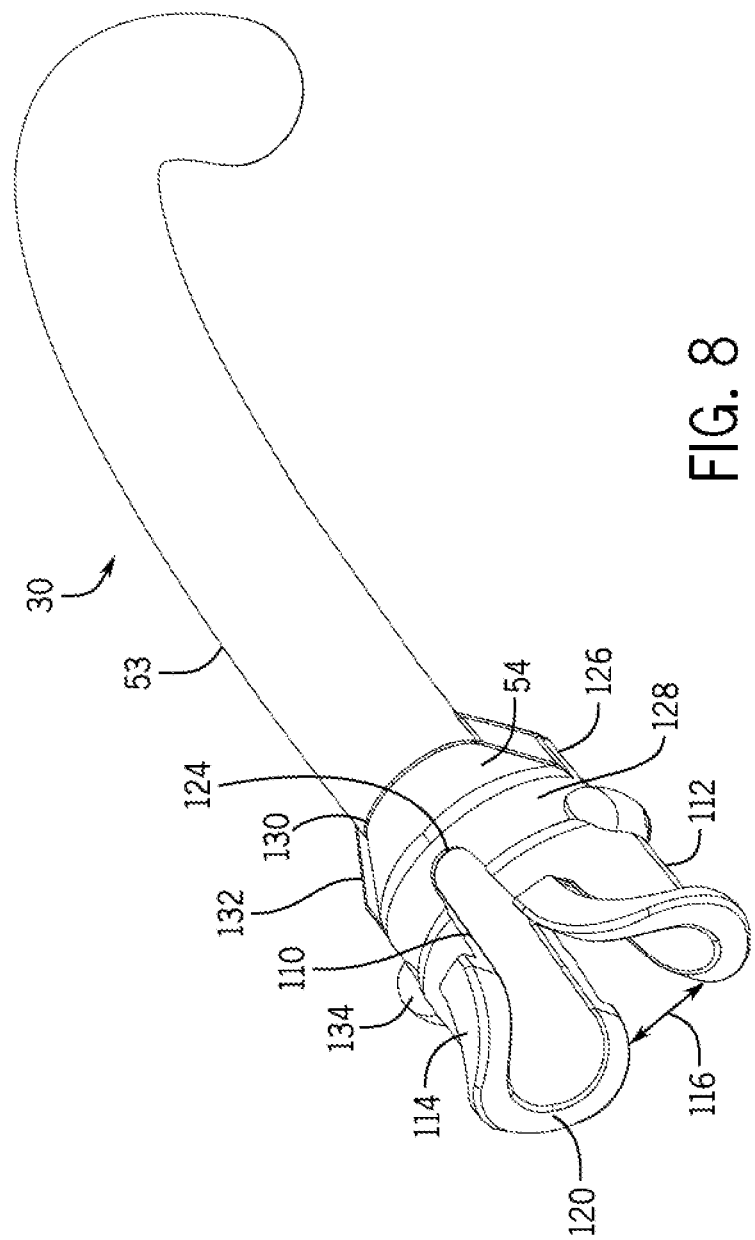

TRACHEOSTOMY TUBE WITH INNER CANNULA

CROSS-REFERENCE TO RELATED APPLICATION

This application claims the benefit of Provisional Application Ser. No. 61/904,319 entitled "Tracheostomy Tube with Inner Cannula, " filed Nov. 14, 2013,which is herein incorporated by reference in its entirety.

BACKGROUND

The present disclosure relates generally to the field of tracheal tubes and, more particularly, to a tracheal tube including an inner cannula with a compressible end and techniques that may be used in conjunction with such tracheal tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of situations exist in which artificial ventilation of a patient may be desired. For short-term ventilation or during certain surgical procedures, endotracheal tubes may be inserted through the mouth to provide oxygen and other gasses to a patient. For other applications, particularly when longer-term intubation is anticipated, tracheostomy tubes may be preferred. Tracheostomy tubes are typically inserted through an incision made in the neck of the patient and through the trachea. A resulting stoma is formed between the tracheal rings below the vocal chords. The tracheostomy tube is then inserted through the opening. In general, two procedures are common for insertion of tracheostomy tubes, including a surgical procedure and a percutaneous technique.

Such tubes may include an inner cannula, such as a reusable inner cannula, or a disposable inner cannula. The inner cannula may be disposed inside the tracheostomy tube and used as a conduit for liquids or gas incoming and outgoing into the patient's lungs. The inner cannula may be removed for cleaning and for disposal of secretions without disturbing the placement of the tracheostomy tube. A connector is typically provided at an upper or proximal end where the tube exits the patient airway, suitable for coupling the ventilator with the inner cannula. In one embodiment, the inner cannula may be removed, cleaned, and reused. In another embodiment, the inner cannula may be disposable, and a new inner cannula may then be positioned inside of the tracheal tube. By enabling the cleaning and/or replacement of the inner cannula, a ventilation circuit may be kept clean and free of secretions.

Standard connectors have been developed to allow the tracheal tube to then be fluidly coupled to artificial ventilation equipment to supply the desired air or gas mixture to the patient, and to evacuate gases from the lungs. One difficulty that arises in the use of tracheal tubes, and tracheostomy tubes in particular, is in the connection of the tube to the ventilation equipment. For example, an inner cannula may not be installed, or may be installed improperly. This may lead to difficulties with ventilation when a connection is made to ventilation equipment.

There is a need, therefore, for improved tracheal tubes, and particularly for improved tracheostomy tubes. It would be desirable to provide a tube that allows for ease of placement and connection of the inner cannula during ventilation.

BRIEF DESCRIPTION

This disclosure provides a novel tracheal tube designed to respond to such needs with a low insertion force and a high retention force. The tracheal tube may be a tube with a separate inner cannula and outer cannula. The inner cannula includes features that allow for ease of insertion into the outer cannula. In certain embodiments, the inner cannula may include features that facilitate gripping of the proximal region and compression prior to insertion. In addition, such features may also facilitate gripping and compression prior to removal. Further, in certain embodiments, the insertion or removal may be done by hand or the tracheal tubes may also be used in conjunction with insertion and/or removal devices that engage with features of the inner cannula.

In contrast to other types of inner cannula connectors, such as threaded or snap-on connectors, the disclosed embodiments may provide inner cannulas that may be inserted and connected in a single movement and that also resist axial or rotational displacement relative to the outer cannula. In particular embodiments, the entire proximal end of the inner cannula, including any cap or lip portion, is smaller in diameter than the widest portion outer cannula connector when properly inserted. In this manner, the outer cannula connector forms the connector portion (e.g., a standard 15 mm connector) for attachment to upstream medical tubing and/or devices. This is in contrast to disposable inner cannulas that, when inserted into an outer cannula and connector, have integral 15 mm connectors. Accordingly, in the disclosed embodiments, the standard connector resides on the outer cannula portion of the tracheal tube, which may allow the outer cannula assembly to be connected to upstream medical tubing with or without an inserted inner cannula.

Further, the compressible end of the inner cannula may be adhered to or otherwise affixed to the inner cannula to form its proximal end region or may be manufactured as a unitary assembly, such as a single molded piece, which may be a cost-effective manufacturing technique. The disclosed tracheal tubes provide improved inner/outer cannula connection while also maintaining standard connections to other medical tubing, such as ventilator tubing.

Thus, in accordance with a first aspect, a tracheal tube assembly includes an outer cannula configured to be positioned in a patient airway. The assembly further includes a flange member secured about the outer cannula and an outer cannula connector coupled to a proximal end of the outer cannula. The assembly further includes an inner cannula configured to be disposed inside the outer cannula such that the inner cannula and the outer cannula are coaxial. The inner cannula features a compressible proximal region that is configured to be positioned at least in part in the outer cannula connector. The compressible proximal region includes a lip configured to be outside of the outer cannula connector when the inner cannula is fully inserted in the outer cannula, wherein the lip is a broken annulus separated by one or more opening or slits in a wall of the proximal end region.

In accordance with another aspect, a tracheal tube system includes an outer cannula configured to be positioned in a patient airway; an inner cannula configured to be disposed inside the outer cannula such that the inner cannula and the outer cannula are coaxial, wherein the inner cannula comprises a compressible proximal region that is configured to be positioned inside the outer cannula connector and wherein the compressible proximal region has a compressed configuration comprising a first diameter when positioned in the outer cannula connector and an uncompressed configuration comprising a second diameter when the compressible proximal region is unbiased and outside of the outer cannula connector; and an insertion or removal device configured to press against an exterior of the proximal region to bias the proximal region into the compressed configuration, wherein the insertion device comprises an opening configured to accommodate the proximal region in the uncompressed configuration.

Also disclosed herein is a tracheal tube assembly that includes an outer cannula configured to be positioned in a patient airway; a flange member secured about the outer cannula; an outer cannula connector coupled to a proximal end of the outer cannula; and an inner cannula configured to be disposed inside the outer cannula comprising: a conduit configured to be inserted into an outer cannula to transfer gas to a patient, the conduit comprising a conduit configured to be inserted into an outer cannula to transfer gas to a patient, the conduit comprising a proximal region, wherein the proximal region is configured to be inserted in an outer cannula connector and wherein the proximal region comprises a protrusion configured to engage with a complementary window or recess in the outer cannula connector.

BRIEF DESCRIPTION OF THE DRAWINGS

Various aspects of the disclosed techniques may become apparent upon reading the following detailed description and upon reference to the drawings in which:

FIG. 2 is a perspective view of the tracheal tube of FIG. 1;

FIG. 3 is a perspective view of a separate inner cannula and outer cannula assembly of the tracheal tube of FIG. 1;

FIG. 4 is a section view of the tracheal tube as in FIG. 1 with the inner cannula inserted in the outer cannula;

FIG. 8 is a top view of a connector region of the inner cannula of FIG. 3;

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort night be complex and time consuming, but would nevertheless be a routine undertaking of design, fabrication, and manufacture for those of ordinary skill having the benefit of this disclosure.

The tracheal tubes as provided herein are disposable rather than reusable, capable of providing differential mechanical ventilation to either or both lungs, and capable of supporting all other functions of standard tracheal tubes (e.g. sealing, positive pressure generation, suctioning, irrigation, drug instillation, etc). The tracheal tubes can be used in conjunction with all acceptable auxiliary airway devices such as (e.g. heat and humidity conservers, mechanical ventilators humidifiers, closed suction systems, scavengers, capnometers, oxygen analyzers, mass spectrometers, PEEP/CPAP devices, etc). Furthermore, although the embodiments of the present disclosure illustrated and described herein are discussed in the context of tracheal tubes such as tracheostomy tubes, it should be noted that presently contemplated embodiments may include a tracheal tube assembly including an inner cannula with a compressible end used in conjunction with other types of airway devices. For example, the disclosed embodiments may be used in conjunction with a single-lumen tube, an endotracheal tube, a double-lumen tube (e.g., a Broncho-Cath™ tube), a specialty tube, or any other airway device with a main ventilation lumen. Indeed, any device with a ventilation lumen designed for use in an airway of a patient may include an inner cannula with a compressible end as provided. As used herein, the term "tracheal tube" may include an endotracheal tube, a tracheostomy tube, a double-lumen tube, a bronchoblocking tube, a specialty tube, or any other airway device.

Figure 1:
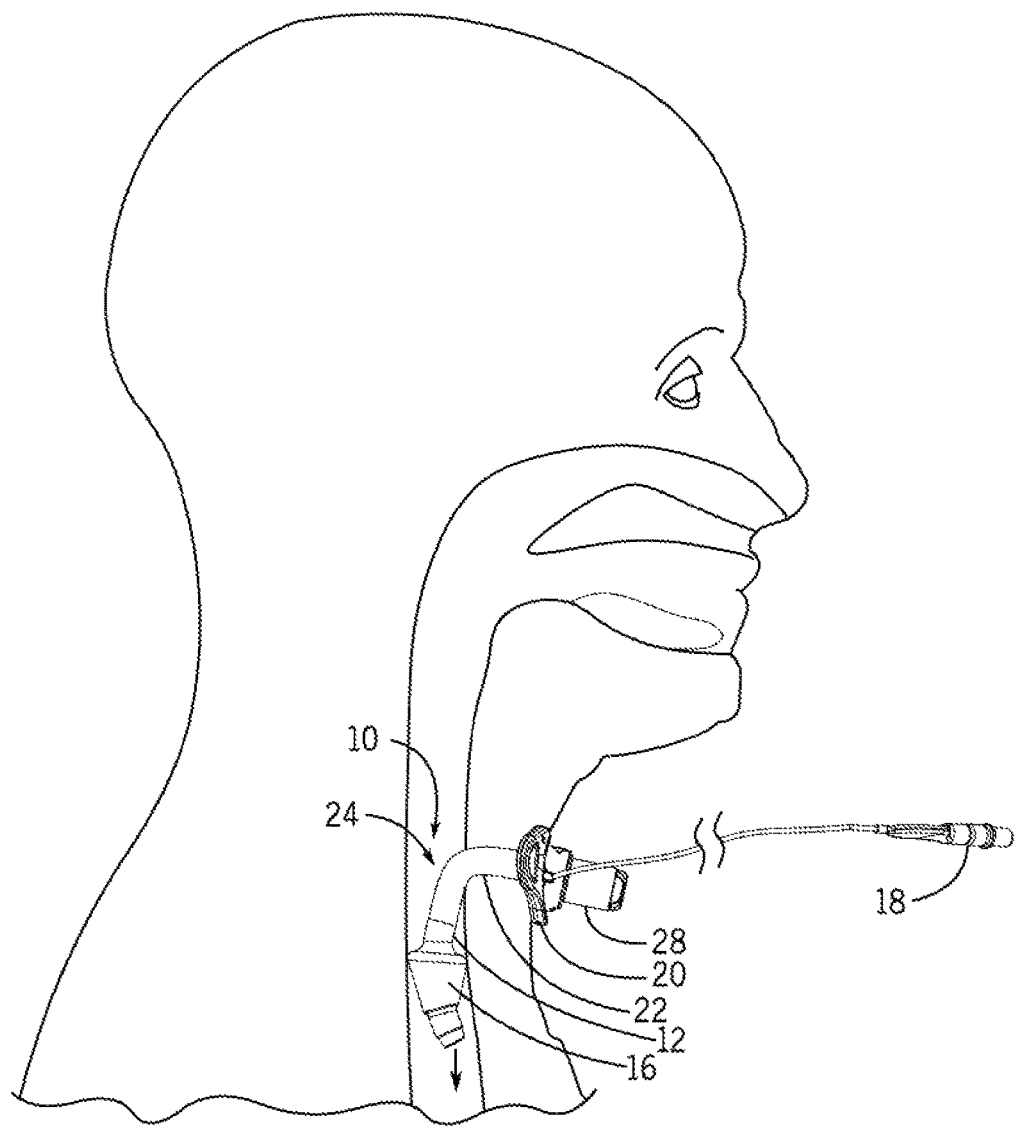
FIG. 1 is a perspective view of a tracheal tube with a compressible inner cannula connector inserted into a patient in accordance with embodiments of the present disclosure.

Turning now to the drawings, FIG. 1 is a perspective view of an exemplary tracheal tube 10 placed in a patient's airway in accordance with aspects of the present disclosure. The tracheal tube assembly 10 represented in the figures is a tracheostomy tube, although aspects of this disclosure could be applied to other tracheal tube structures, such as endotracheal tubes. The application to a tracheostomy tube is apt, however, insomuch as such tubes tend to be worn for longer periods of time and, thus, may include a removable and/or disposable inner cannula disposed inside of an outer cannula 12, which is useful in maintaining a clean ventilation circuit.

The tracheal tube 10 includes an outer cannula 12 that defines a ventilation lumen and that facilitates the transfer of gases to and from the lungs. The tracheal tube 10 includes an inflatable cuff 16 disposed on the outer cannula 12. However, certain embodiments of the disclosure may be used in conjunction with cuffless tubes. A proximal end of the tracheal tube 12 may connect to upstream airway devices (e.g., a ventilator) via the appropriate medical tubing and/or connectors. In embodiments that include a cuff 16, a pilot balloon and inflation line assembly 18 is coupled to the cuff 16.

The outer cannula 12 is illustrated extending both distally as well as proximally from a flange member 20. A pair of side wings of the flange 20 extend laterally and serve to allow a strap or retaining member (not shown) to hold the tube assembly 10 in place on the patient. In one embodiment, apertures formed in each side of the flange member 20 allow the passage of such a retaining device. In many applications, the flange member 20 may be taped or sutured in place as well. During intubation, the tracheal tube assembly 10 is placed through an opening formed in the neck and trachea of a patient and extending into the patient airway. In certain embodiments, the tracheal tube assembly 10 is curved to accommodate the curved tracheal passageway. For example, the outer cannula 12 may be curved in an unbiased state (i.e., outside the patient) such that an inner curve 22 is generally positioned on a ventral side of the patient while the outer curve 24 is positioned on the dorsal side of the patient when the tracheal tube assembly 10 is inserted in the patient. Further, while a distal portion of the outer cannula 12 is inserted within the patient, a proximal portion of the outer cannula 12 forms an outer cannula connector 28. As provided herein, the outer cannula connector 28 receives a proximal end region of the inner cannula and forms a secure connection.

FIG. 2 is a perspective view of the tracheal tube assembly 10 showing an inner cannula 30 inserted in the outer cannula 12 and forming a connection with the outer cannula connector 28. The proximal end region 32 is disposed within the outer cannula connector 28 such that a proximal end 34 is exposed (i.e., is not within the outer cannula connector 28). The inner cannula 30 is generally coaxial with the outer cannula 12 and is shaped to fit within the outer cannula 12 to form the gas conveying passageway to the patient. In this manner, the inner cannula 30 may be removed and replaced while the outer cannula 12 is retained. This reduces stress on the stoma wile permitting cleaning of the passageway. The outer cannula connector 28 may feature a stepped or thicker coupling portion 29 to couple the connector 28 to the flange member 20, which extends away from the outer cannula connector 28 into opposing wing members 31, each including tie holes 33. In one embodiment, an imaginary axis or line connecting the tie holes 33 may be the direction of compression for the proximal end region 32, as discussed herein.

In certain embodiments of the present techniques, the inner cannula 30 may be manually inserted into the outer cannula 12. As shown in FIG. 3, the inner cannula 30 may be inserted by pushing the distal end 40 through the proximal end 44 of the outer cannula 12, e.g., in the direction of arrow 46. The insertion is complete when the distal end 40 is generally located at or near the distal end 48 of the outer cannula 12. In certain embodiments, the distal end 40 of the inner cannula 30 terminates short of the distal end 48 of the outer cannula and is disposed entirely within the outer cannula. When the inner cannula 30 is fully or suitably inserted to facilitate patient ventilation, the proximal end region 32 is disposed at least in part within the outer cannula connector 28. In embodiments in which the outer cannula forms a curve, such as a Magill curve, the inner cannula 30 may also be curved in a complementary fashion. Accordingly, the insertion may be directional such that proper insertion involves an inner curve 50 of the inner cannula 30 located proximate to or corresponding with the inner curve 22 of the outer cannula 12. Similarly, the outer curve 52 of the inner cannula 30 will be located proximate to the outer curve 24 of the outer cannula 12. The positioning of the inner cannula 30 in the outer cannula 12 may be facilitated by operator technique and, in particular embodiments, with the aid of markings, instructions, or other visual indicators.

The inner cannula 30 forms a conduit from which liquids or gases, including medications, may enter through the proximal end 34. As depicted, the proximal end region 32 forms part of the connector region of the inner cannula 30, while an inserted portion 53 forms most of the main body of the inner cannula 30. The inserted portion 53 that extends into the patient airway to the distal end 40 is coupled to a narrowing or tapered region 54 of the proximal end region 32 and is generally sized and shaped to facilitate insertion within the main body of the outer cannula 12. Both the inner cannula 30 and the outer cannula 12 have dimensions selected to fit easily through the stoma. In practice, a range of such tubes may be provided to accommodate the different contours and sizes of patients and patient airways. Such tube families may include tubes designed for neonatal and pediatric patients as well as for adults. By way of example only, the outer cannula 12 of the tube 10 may range from 4 mm to 16 mm. The inner cannula 30 may be sized to correspond with an appropriate outer cannula 12. The outer cannula 12 and the inner cannula 30 may be characterized by their inner diameters (referring to the diameter of the interior of the passageway) or their outer diameters (referring to the diameter as measured from the exterior outside wall to exterior outside wall).

Because the inner cannula 30 fits within the outer cannula 12, the outer cannula 12 features a larger inner diameter 60 relative to an outer diameter 64 of the inserted portion 53 of the inner cannula 30. The outer diameter 64 of the inserted portion 53 of the inner cannula 30 may be selected to allow sufficient air flow while also fitting comfortably within the outer cannula 12 and allowing for appropriate insertion force. The inner diameter of the outer cannula 30 is less than the outer diameter 64 by the thickness of the walls of the inner cannula 30. For example, an inner cannula 30 sized to 6.5 mm may have an outer diameter 64 of about 6.5 mm and an inner diameter of about 5.5 mm. In such an embodiment, the inner cannula walls are about 1 mm thick in the inserted portion of the inner cannula 30 (e.g., in portions distal of the proximal end region 32). Similarly, a 10 mm inner cannula 30 may have an inner diameter of about 9 mm. Accordingly, tubes sized to 6.5 mm, 7.0 mm, 7.5 mm 8.0 mm, 8.5 mm, 9.0, or 10 mm may feature smaller inner diameters that define the airflow passage.

Further, the inner diameter 62 at the proximal end 44 of the outer cannula 12 is typically larger than the inner diameter 60 and is selected to couple to appropriate tubing. That is, the outer cannula 12 is narrower in the inserted portion and is wider at the connector. The proximal end region 32 also has a larger outer diameter 70 relative to the inserted portion 53. In certain embodiments, the proximal end region may flare or taper outwards gradually such that the diameter increases gradually, with the largest diameter 70 at the proximal end 34. In other embodiment, the proximal end region 32 may include a generally barrel-shaped region with an outer diameter 70. It should be understood that the proximal end region 32 may change under compression. Accordingly, the outer diameter 70 refers to the uncompressed configuration. Further, in embodiments in which the proximal end 34 forms a broken annulus (i.e., is not a continuous element), the outer diameter 70 refers to a diameter between the solid portions of the proximal end 34. When the proximal end region 32 is within the outer cannula connector 28, the outer cannula connector 28 provides a biasing force that compresses the proximal end region 32 into a compressed configuration that is sized to fit within the inner diameter 62 of the outer cannula connector 28. The outer diameter 70 is larger than a largest outer diameter of the inner cannula 30 in the compressed configuration.

FIG. 4 is a section view of an inner cannula 30 positioned within the outer cannula 12. When the inner cannula 30 is in the compressed configuration, the proximal end region 32 is constrained by the wall 82 of the outer cannula connector 28. Accordingly, the outer diameter 84 is smaller than the outer diameter 70 (see FIG. 3) of the uncompressed configuration. In one embodiment, the outer diameter 84 is about 15 mm or slightly smaller. That is, uncompressed outer diameter 70 is about the outer diameter of a 15 mm connector. The resulting proximal opening 86 of the inner cannula 30 is also smaller. In a specific embodiment, the material of the proximal end region 32 is selected so that an operator is capable of changing the configuration of the proximal end region 32 through the application of a biasing force. Similarly, the wall 82 of the outer cannula connector 28 is sufficiently strong to maintain the proximal end region 32 in the compressed configuration.

The outer cannula connector 28 may be formed in accordance with industry standards to permit and facilitate connection to ventilating equipment (not shown). By way of example, the outer cannula connector 28 is a 15 mm connector, although other sizes and connector styles may be used. Additionally, the tracheal tube assembly 10 may be connected to other medical devices, such as a suction device, a T-junction, a medicine delivery system, and so forth. Indeed, the outer cannula connector 28 may enable the attachment of one or more medical devices to the tracheal tube assembly 10. To accommodate such a connection, the proximal end region 32 may be formed such that, when inserted, the inner cannula 30 does not interfere with coupling via the outer cannula connector 28. To that end, in particular embodiments, the widest diameter 84 of the inner cannula 30, including any protruding portions, is smaller than the widest outer diameter (e.g., 15 mm) of the outer cannula connector 28. It should be understood that, the inserted portions of the proximal end region 32 press against the wall 82 of the outer cannula connector 28 and feature an outer diameter that is slightly smaller (e.g., 12 mm or smaller) than the inner diameter of the outer cannula connector 28. Further, the inner cannula 30 may feature regions with different outer diameters along its length in either configuration.

Because the inner cannula 30 is configured to be inserted and/or removed by an operator, the proximal end 34 may protrude from the outer cannula connector 28 to allow the proximal end region 32 to be manipulated while the inner cannula 30 is in place. For example, the proximal end 34 protrudes proximally or along a rotational axis 87 of the outer cannula connector 28. The axis 87 is generally orthogonal to the axis 88 along a longest dimension of the flange member 20. When inserted in the patient, the inner cannula. 30 may be positioned so that the operator grips the proximal end and pushes laterally (e.g., along the axis 88).

Figure 5:
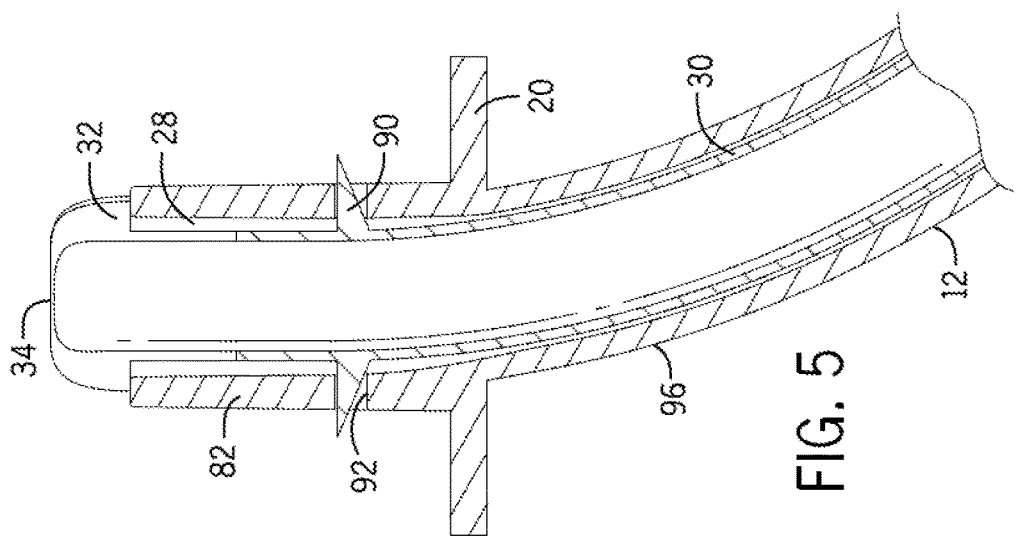
FIG. 5 is a section view of an embodiment of an inner cannula inserted into an outer cannula with anti-rotation engagement features in accordance with embodiments of the present disclosure.

In addition to a compressible connector portion (e.g., the proximal end region 32) of the inner cannula 30, the inner cannula 30 may also include features that engage with the outer cannula 12 and/or the outer cannula connector 28 to promote alignment and prevent rotation or dislodgement of the inner cannula 30 relative to the outer cannula 12. As shown in FIG. 5, which is a sectional view of an inner cannula 30 coupled to an outer cannula 12, the inserted portion 53 includes latches 90 that engage with complementary windows 92 through the wall 82 of the outer cannula connector 28. In the depicted embodiment, the latches 90 may be sized at shaped to extend beyond the windows 92 such that the latches 90 protrude from the wall 82. In other embodiments, the latches 90 may be flush with or recessed within the wall 82, depending on the size and shape of the latch 90. Further, in embodiments in winch the windows 92 extend completely through the wall 82, the engagement of the latches 90 is visible from the exterior of the outer cannula connector 28, providing a visual check for proper alignment.

In embodiments in which the latches 90 are not disposed on the compressible proximal end region 32, the latches 90 may be formed from a compliant material that compresses or bends to allow progress if the inner cannula 30 within the outer cannula connector 28. Upon encountering the windows 92, the latches may then assume an uncompressed configuration. In one embodiment, the latches 92 may be hollow barbs. Further, the latches may also be shaped to point or curve generally towards the proximal end 34 to encourage smoother progress of the inner cannula 30 within the outer cannula connector 28.

In certain embodiments, the latches 90 may be positioned on the inner cannula 30 to be within the inner cannula connector 28 and not the more distal portion inserted portion 96 of the outer cannula 12. In one embodiment, the latches 90 may be positioned opposite one another about the circumference of the inner cannula 30. In the depicted embodiment, the latches 90 are aligned with the wings of the flange member 20. Such positioning may be advantageous in embodiments in which the compression and decompression of the proximal end region 32 is also along an axis connecting the wings of the flange member 20. Although the latches 90 may not be directly compressed upon compression of the proximal end region 32, the material of the inserted portion 53 may nonetheless bend or compress slightly in areas of the inner cannula. 30 adjacent to and aligned with the compression points to allow smoother insertion of the protruding latches 90.

Figure 7:
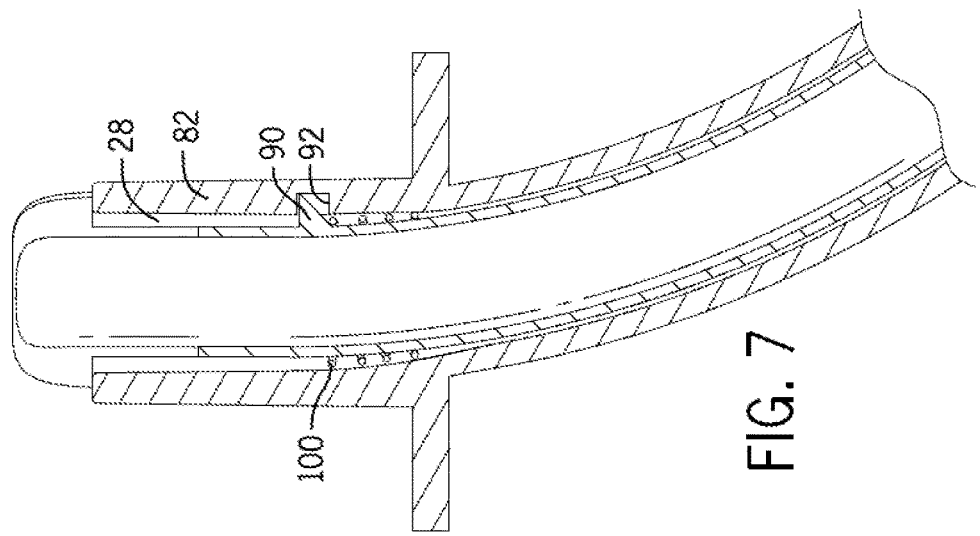
FIG. 7 is a section view of an alternative embodiment of an inner cannula inserted into an outer cannula with a single anti-rotation engagement feature and a spring-loaded length adjustment feature in accordance with embodiments of the present disclosure.
Figure 6:
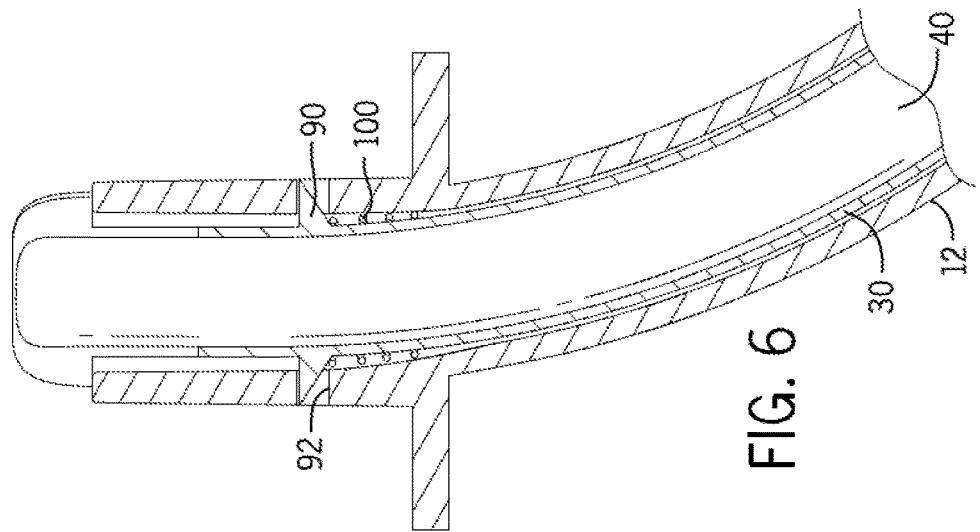
FIG. 6 is a section view of an embodiment of an inner cannula inserted into an outer cannula with anti-rotation engagement features and a spring-loaded length adjustment feature in accordance with embodiments of the present disclosure.

FIG. 6 is an alternate embodiment in which the inner cannula 30 includes a spring 100 to facilitate alignment of the latches 90 within the windows 92. The spring 100 may be integral with the body of the inner cannula 30 in just a portion of its length. Compression of the spring towards the distal end helps move the latches 90 distally. The spring 100 may be positioned adjacent to the latches 90, either on a proximal or distal side. FIG. 7 shows another embodiment with a single latch 90 that engages with a window 92 that does not extend completely through the wall 82 of the outer cannula connector 28. Such an embodiment may permit a smaller-sized latch 92, which may allow a lower cannula insertion force. Further, such an embodiment may be used when the latch 90 is positioned to align with the coupling portion 29 (see FIG. 2) of the outer cannula connector 28. While the depicted embodiment is implemented in conjunction with the spring 100, it should be understood that the spring 100 may also not be used.

FIG. 8 is a perspective view of an inner cannula 30 in the uncompressed configuration. In the depicted configuration, the proximal end 34 assumes its largest unbiased outer diameter 70. Further, in the depicted embodiment, the inner cannula 30 includes a plurality of opening 110 that facilitate compression. When force is applied to compress the first ear 112 and the second ear 114, these structures move towards one another (e.g., along axis 88, see FIG. 4) and the gap 116 formed by the openings 90 decrease as the proximal end region 32 assumes the smaller, compressed outer diameter 84 (see FIG. 4). For example, an application of 5N of force or less may be applied to achieve sufficient compression to insert the inner cannula 30. In other embodiments, the proximal end region 32 may form a single gripping structure (e.g., may have no opening 110) or more than two ears.

The opening 110 allows the proximal end 34 of the inner cannula 30 to form a smaller compressed diameter 84 under a compression force without wrinkling and while maintaining a generally circular cross-section over the inserted portion of the proximal end region 32 that corresponds with the generally circular cross-section of the outer cannula connector 28. The size and number of openings 110 may be selected according to the size and manufacturing of the inner cannula 30. In one embodiment, the proximal end region has two openings 110. In embodiments with only one opening 110, the size of the gap 116 in the uncompressed configuration may be relatively larger to facilitate the change from uncompressed to compressed with fewer openings. Further, the openings 110 may be differently-sized relative to one another. The size of the gaps 116 may be measured in either the compressed or the uncompressed configuration, and may be a largest space between the adjacent portions of the inner cannula wall 120.

In the depicted embodiment of an inner cannula 30 including one or more openings 110, the opening 110 may terminate at a furthest distal terminus 124. The more distal the distal terminus 124 is, the greater the degree of compression of the proximal end region 32. Accordingly, in certain embodiments, it may be desirable to include at least one elongated opening 110 to achieve more compression. For example the distal terminus 124 may be positioned at least to be at of more distal than the junction 126 between a more barrel-shaped region 128 and the tapered region 54. In other embodiments, the distal terminus 124 may be positioned within the tapered region 54 between the junction 126 and a junction 130 between a narrowest point of the tapered region 54 and the inserted portion 53. In this manner, greater compression of any protruding features may be achieved, including, e.g., support ribs 132 and mating features, such as protrusions 134. Further, the distal terminus 124 may be rounded, as depicted, or may be the tip of a V-shaped opening 110 for even greater potential compression.

The openings 110 may be positioned to correspond with a dorsal and ventral side of the tube 10 (e.g. to correspond with the inner curve 50 and the outer curve 52 of the inner cannula, see FIG. 3) when inserted to encourage lateral compression. In other embodiments, the openings 110 may be positioned to laterally to facilitate compression along a dorsal-ventral axis.

Figure 9:
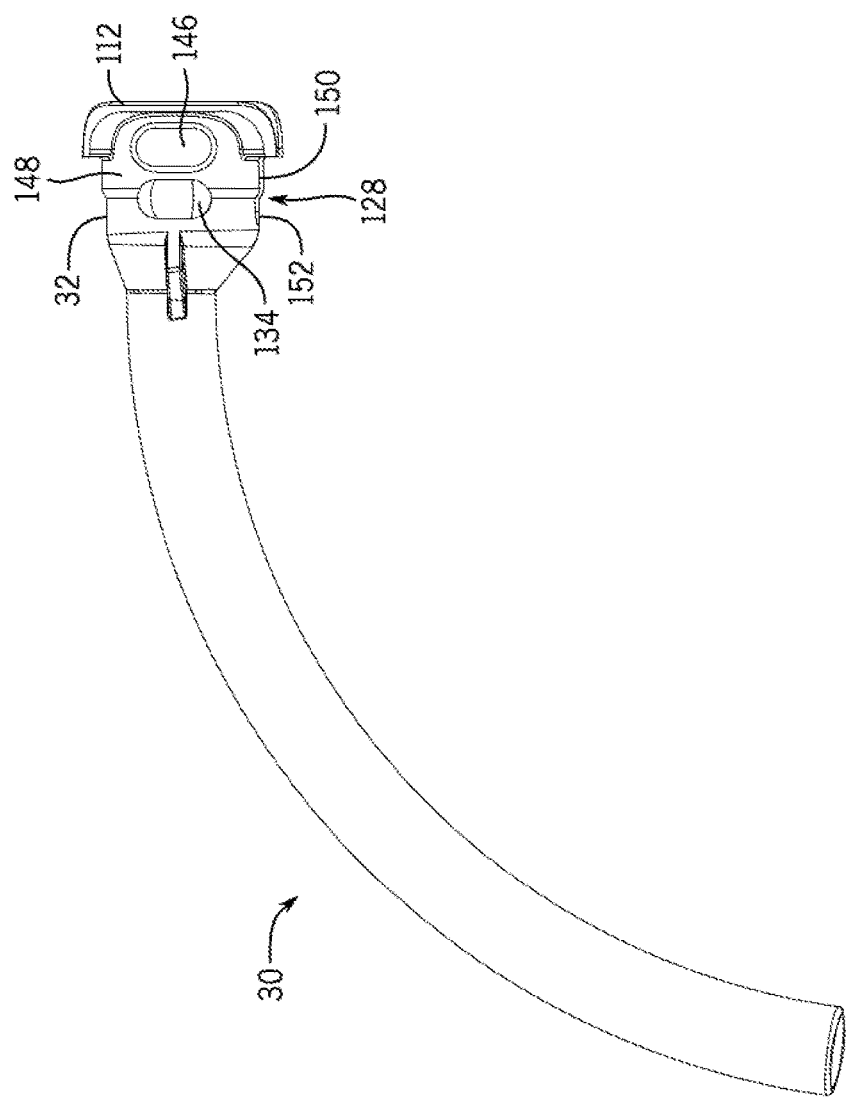
FIG. 9 is a side view of a connector region of an inner cannula including an opening on a compressible ear or wing.

FIG. 9 is a side view of an alternate configuration of proximal end region 32 that includes one or openings 146. The openings 146 may provide an improved gripping surface on one or more ears, e.g., ear 112. As depicted, the opening 146 is aligned with the protrusion 134. Where the protrusion 134 may impede gripping device or finger, the opening may provide increased space for a finger to find purchase on the exterior surface 148 of the proximal end region 32. Further, in embodiments in which the more proximal portion 150 of the barrel-shaped region 128 has a slightly wider diameter relative to the adjacent portion 152, the openings 146 provide more space into which the wall 120 of the inner cannula 30 can compress (e.g., in multiple directions) under force.

Figure 10:
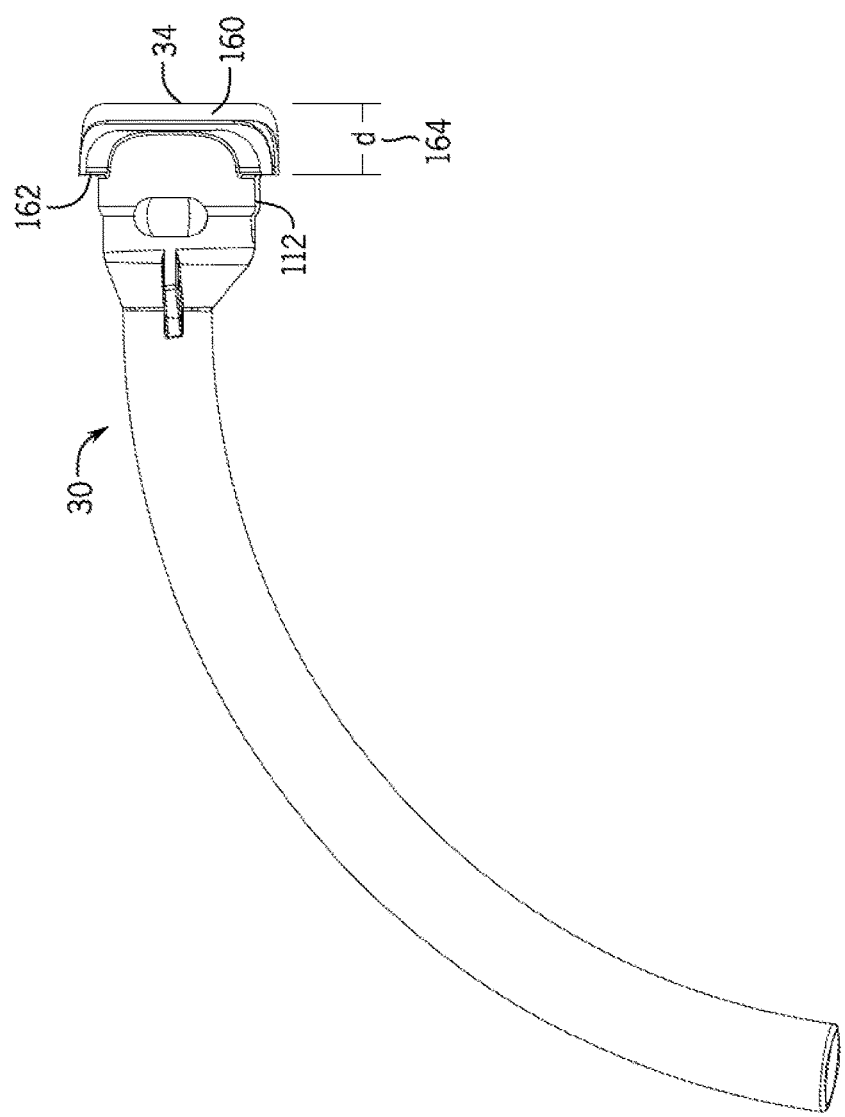
FIG. 10 is a side view of a connector region of an inner cannula including an expanded lip region.

The proximal end 34 may also terminate in a lip 160 that is formed in the wall 120, shown in FIG. 10. The relatively thicker lip 160 may also extend at least partially towards the distal terminus 124 and may further include an abutment surface 162. The abutment surface 162 is configured to abut the proximal end 44 of the outer cannula connector 28 and prevent further movement of the inner cannula 30 distally, which may assist in aligning the inner cannula 30 within the outer cannula 12. In certain embodiments, a distance 164 from the abutment surface 162 to the proximal end 34 is less than a distance from the proximal end 34 to the distal terminus 124 (see FIG. 8). In particular embodiments, the distance 164 is less than 50% of the distance from the proximal end 34 to the distal terminus 124. In a particular embodiment, the distance 164 is about 4 mm. Further, in another embodiment, the proximal lip 160 may be about 2.7 mm or more in thickness. During, insertion, although an operator may grip the proximal end region 32 more generally, as more of the inner cannula 30 is positioned within the outer cannula 12, eventually the available gripping surface decreases. The proximal lip 160 provides gripping surface for the operator during the entire insertion.

Figure 11:
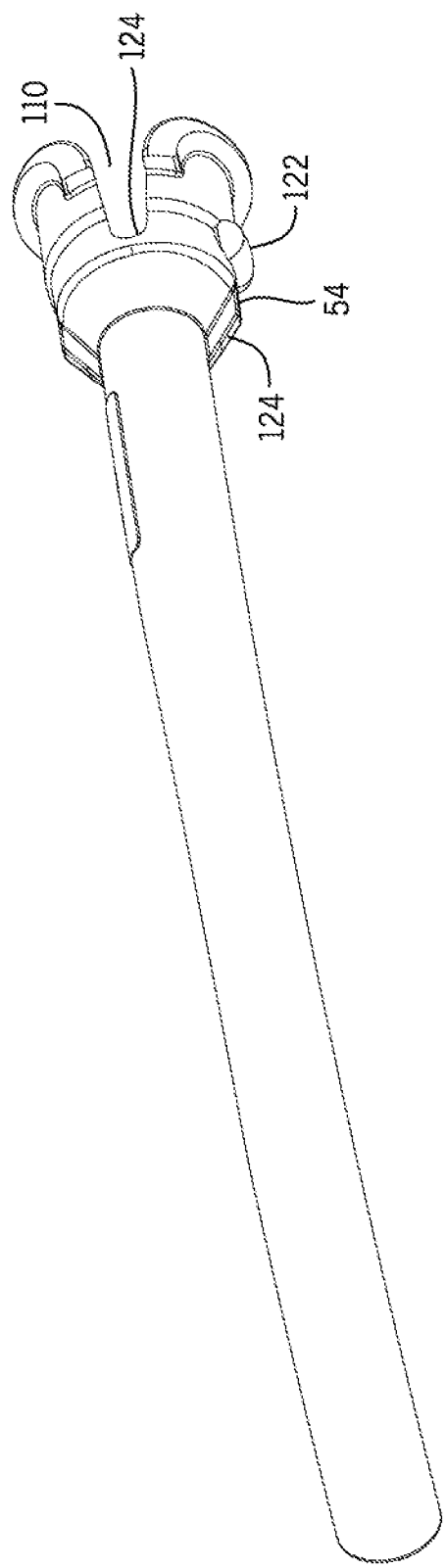
FIG. 11 is a top view of a connector region of an inner cannula including only one engagement feature.

As noted, in particular embodiments, the proximal end region 32 may include mating features that couple to complementary features on the interior wall of the outer cannula connector 28 (see FIG. 4). Such mating features may prevent rotational movement of the inner cannula 30 relative to the outer cannula connector 28. In addition, the mating features may provide additional alignment to facilitate correct alignment of the curve of the inner cannula 30 with the curve of the outer cannula 12 (see FIG. 3). As depicted in FIG. 11, the mating features may be protrusions, such as protrusion 134 formed on an exterior surface 120 of the inner cannula. 30 in the proximal end region 32. The protrusion 134 may be formed in any suitable shape or combination of shapes, such a rounded bump, a ramp shape, a pyramid structure, etc. Further, the proximal end region 32 may include any number of protrusions 134 positioned about a circumference. For example, the proximal end region 32 may include two protrusions 134 that oppose one another. In specific embodiments, opposing protrusions 134 may be circumferentially centered on the ears 112 and 114. In such embodiments, the protrusions 134 may serve as guides for an operator to press against to bias the ears 112 and 114 towards one another. In another embodiment, the protrusions 134 may be about 90 degrees from opposing notches 90. In another embodiment, respective protrusions 134 may be provided as a partial ring with an arc having less than 45° of circumference of the proximal end region 32. In another embodiment, the protrusion 134 may form a ring about the circumference of the proximal end region 32.

It should be understood that the mating features may also be implemented as recesses or a combination of protrusions and recesses. The size of the protrusion 134 may be selected to fit into it corresponding recess in the outer cannula connector 28 and may be less than a thickness of the wall of the outer cannula connector 28. In one embodiment, the protrusion 134 may protrude less than about 1 mm, less than about 1.5 mm or less than about 2 min from the exterior surface 120. In particular embodiments, the protrusions 134 protrude less than a widest diameter 70 in an uncompressed configuration. Alternatively, the protrusion 134 may fit into complementary windows formed in the outer cannula connector. In such embodiments, the protrusion 134 may be larger. The inner cannula 30 may also include additional support structures, such as one or more ribs 132. In the depicted embodiment, the rib 132 may provide structural support to the protrusion 134. In addition, the tapered region 54 may be formed proximate to the protrusion 134 to facilitate insertion of the relatively larger protrusion 134 into the inner cannula connector 28.

FIG. 11 is a top view of the inner cannula connector having a single protrusion 134. Such an embodiment may be associated with a lower insertion force for the inner cannula 30, as the protrusions 134 may increase friction along the interior of the inner cannula connector 28. Further, a single protrusion 134 may be more readily aligned with a single complementary recess formed on the interior of the inner cannula connector 28. In certain embodiments, the protrusion/s 134 may be positioned to align with the distal terminus 124 of an opening 110. In other embodiments, the protrusions may be positioned to be proximal of the distal terminus 124.

Figure 12:
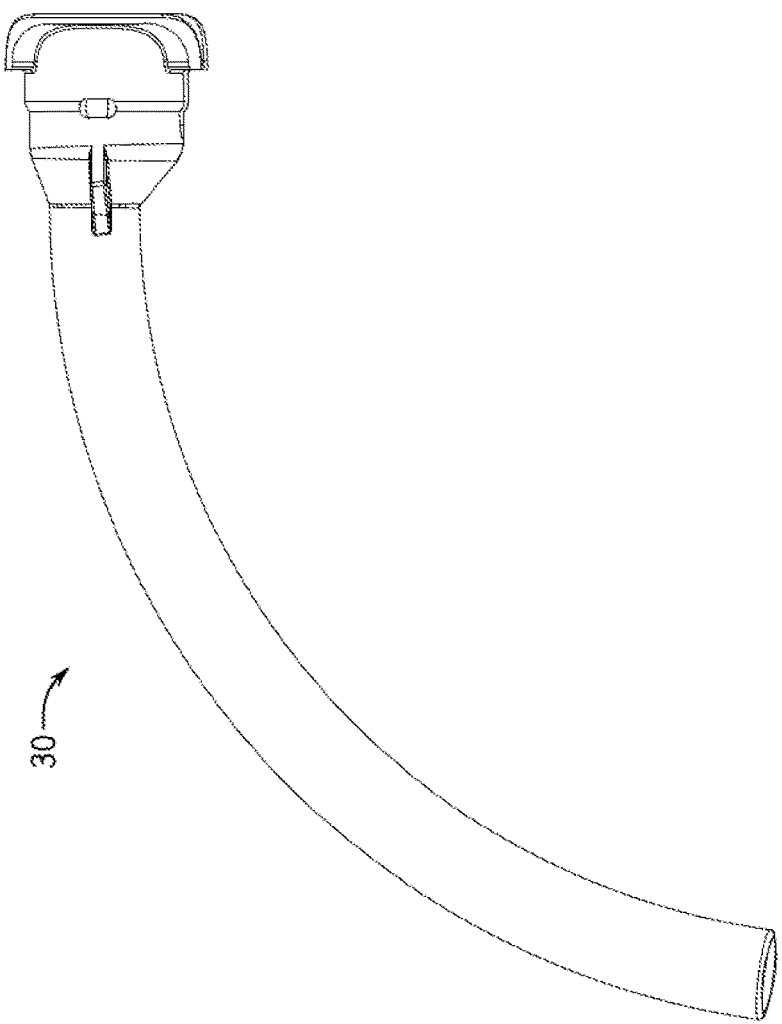
FIG. 12 is a side view of a connector region of an inner cannula including a reduced size engagement feature.
Figure 13:
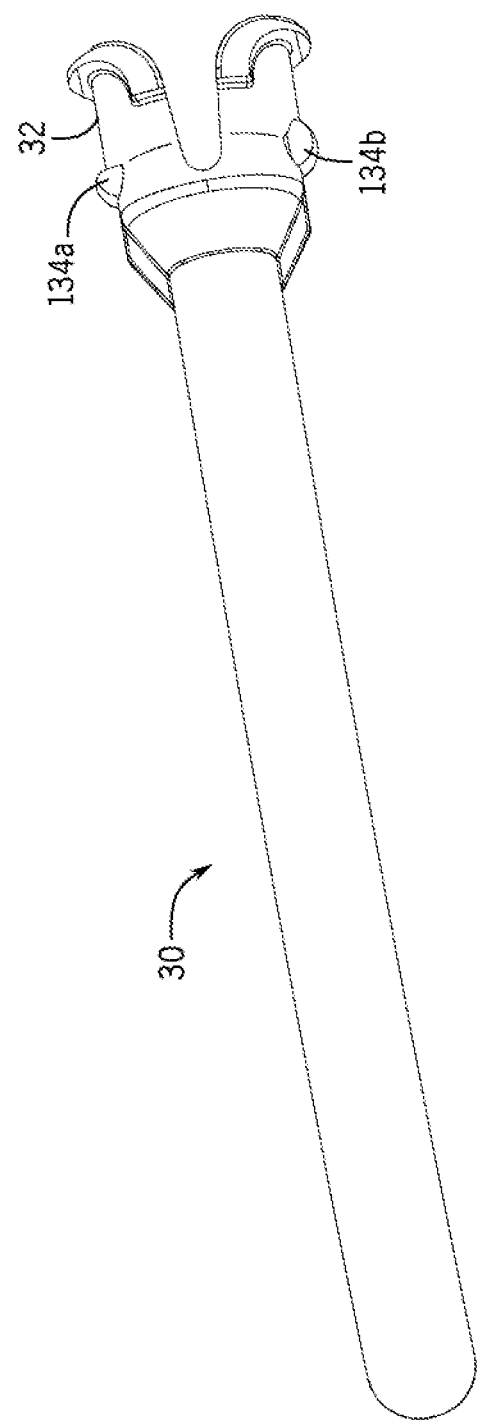
FIG. 13 is a top view of a connector region of an inner cannula including a distally-weighted engagement feature.
Figure 14:
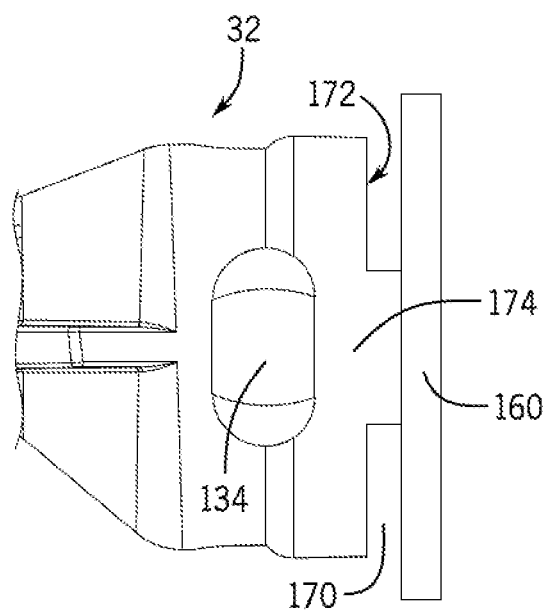
FIG. 14 is a partial side view of a connector region of an inner cannula including a separated lip region.

FIG. 12 is an alternate embodiment showing a protrusion 134 with a reduced surface area and volume relative to the protrusion 134 of FIG. 11. The size of the protrusion 134 may be related to the insertion force involved in correctly positioning the inner cannula 30 within the outer cannula connector 28. Larger protrusions 134 may have larger insertion forces. The depicted embodiment may be used to achieve a lower insertion force, for example for inner cannulas 30 sized for pediatric use. In particular embodiments, protrusions 134 may be differently-sized and/or shaped depending on their inner diameter. The complementary recess on the outer cannula connector 28 may also be sized to only accept an inner cannula 30 having a protrusion 134 of a certain size and/or shape, thus reducing the possibility of having an incorrectly-sized inner cannula 30 inserted. In one embodiment, the protrusions 134 may increase as the inner diameter of the inner cannula 30 increases, allowing a quick visual confirmation for the operator that a larger or smaller inner cannula 30 has been selected from a collection of cannulas of multiple sizes. FIG. 13 is another alternate embodiment showing a protrusion 134a with only a more proximal half of its volume removed relative to its opposing protrusion 134b. Removal of protruding volume in the wider diameter portion of the proximal end region 32 may facilitate insertion of the inner cannula. 30 with lower insertion forces. While the depicted embodiment shows the protrusions 134a and 134b being asymmetrically-sized, it should be understood that one or all of the protrusions 134 may be configured to position a majority of the protruding volume more distally relative to symmetrically-configured protrusions 134.

Figure 15:
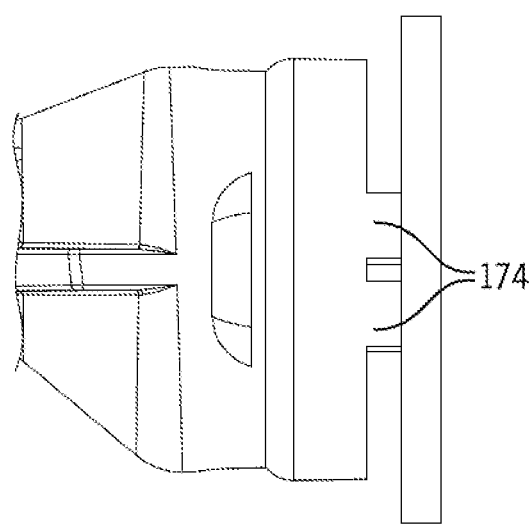
FIG. 15 is a partial side view of a connector region of an inner cannula including a separated lip region with a double-rib support.

The proximal end region 32 may also include additional features to enhance insertion of the inner cannula 30. FIGS. 14-19 depict various embodiment of proximal end regions 32 including cutouts 170 that separate the proximal lip 160 from the adjacent section 172. The cutouts 170 may be positioned to form short arc or longer arcs about the circumference of the proximal end region, and may be present in any suitable number. The cutouts 170 are separated by one or more support pillars 174. Further, the proximal end region 32 may or may not include any openings 110. If one or more openings 110 are present, the cutouts 170 may be positioned within one or more of the ears 112 and 114. If no openings 110 are present, in one embodiment, the cutout 170 may be a single almost complete annulus interrupted by a support pillar 174. In this manner, the proximal lip 160 may form a hinged pull ring that may pivot away from the proximal end region to facilitate removal of the inner cannula 30. FIG. 15 is an alternate embodiment in which the proximal end region 32 includes two support pillars 174 spaced apart from one another to reinforce the strength of the hinged connection with the proximal lip 160. Further, the particular features of the inner cannula 30 may be combined or exchanged with one another. In the depicted embodiment, the protrusion 134 is also reduced in size to facilitate insertion.

Figure 16A:
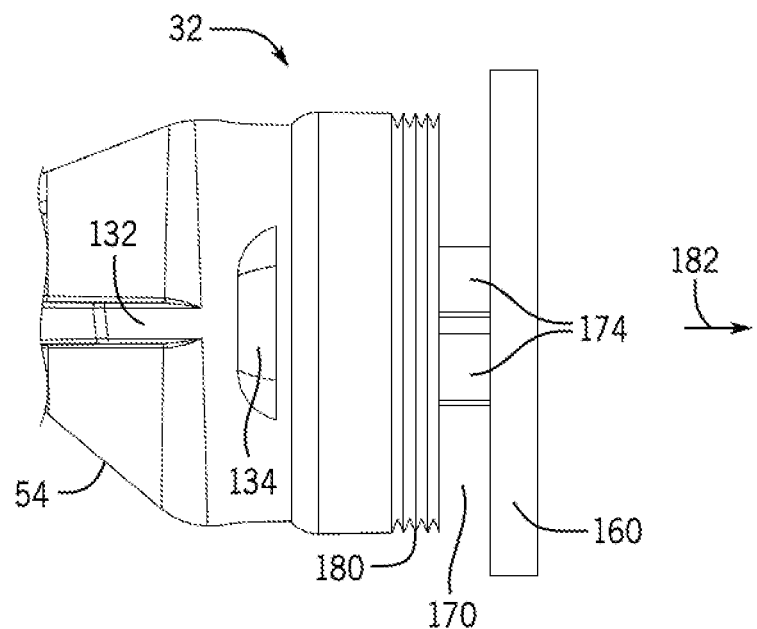
FIG. 16A is a partial side view of a connector region of an inner cannula including a corrugated region.
Figure 16B:
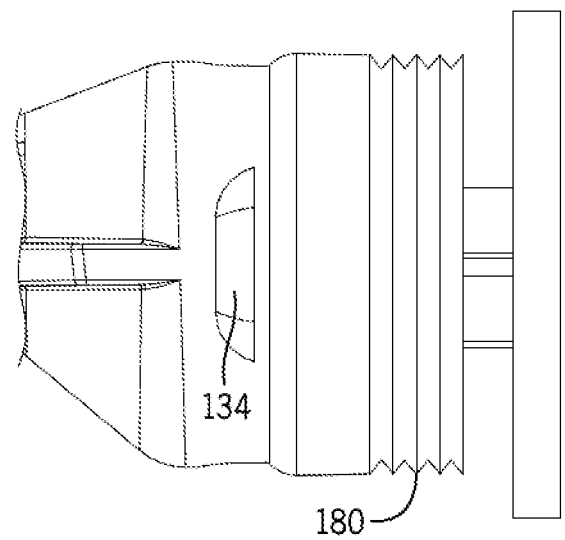
FIG. 16B is a partial side view of the connector region of FIG. 16A showing the corrugated region when expanded.

In other embodiments, as shown in FIGS. 16A and 16B, the proximal end region may include a bellows 180 configured to expand when a force is applied in the direction of arrow 182, shown in FIG. 16A. In this manner, the proximal lip 160 moves away from the outer cannula connector 28 to allow more room for a finger or other device to grasp the proximal lip and remove the inner cannula. The cutouts 170 also allow additional room to facilitate engagement with the proximal lip 160. FIG. 16B shows the bellows 180 in the expanded configuration. For example, the bellows 180 may expand from about a 4 mm size (including a distance from the bellows 180 to the proximal lip 160) to a 10 mm size. The bellows 180 may be formed integrally with the material of the proximal end region 32. For example, the bellows 180 may be formed by molding a corrugated section into the proximal end region during, manufacturing. In addition, to accommodate the bellows 180, any protrusions 134 present may be located relatively distally (e.g., adjacent to the junction with support ribs 132) or may be reduced in size.

Figure 17:
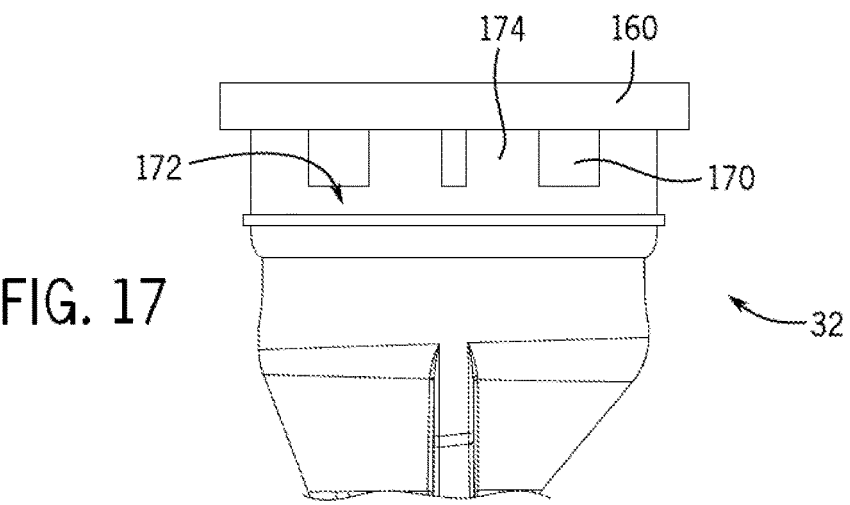
FIG. 17 is a partial side view of a connector region of an inner cannula including a separated lip region with slotted supports.
Figure 18:
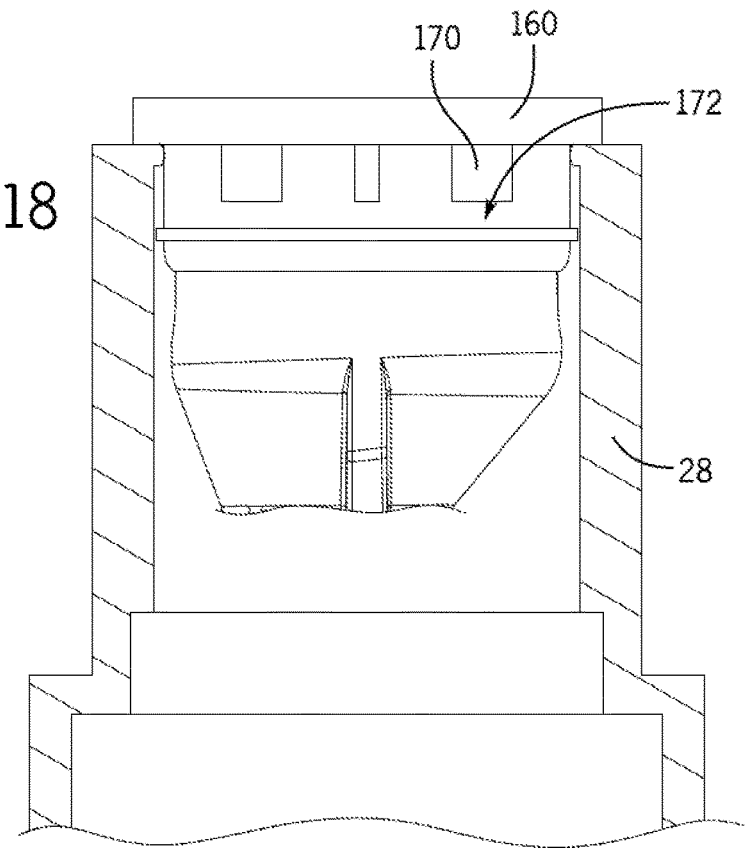
FIG. 18 is a partial section view of the connector region of FIG. 17 with the slotted supports positioned in an outer cannula connector.
Figure 19:
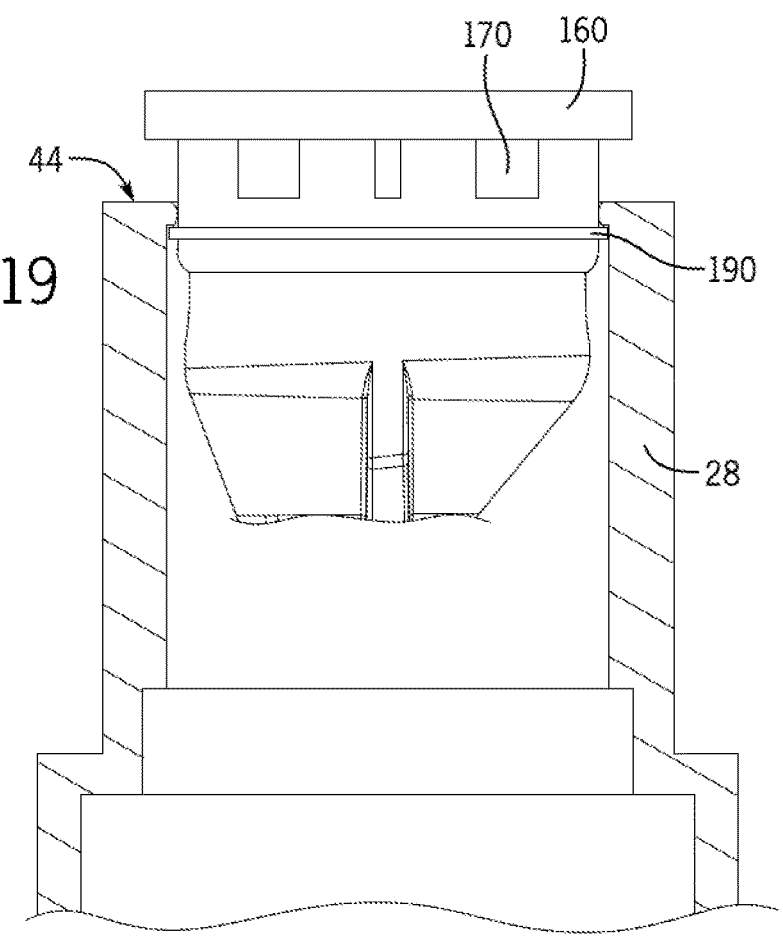
FIG. 19 is a partial section view of an alternative connector region with the slotted supports positioned outside an outer cannula connector.

As shown in FIG. 17, the proximal end region 32 may include any suitable combination of cutouts 170 and support pillars 174. Further, while certain embodiments may yield a proximal lip 160 coupled to the adjacent section 172 via a single hinge, the proximal lip 160 may still function as a pull ring even when coupled to the adjacent section 172 at multiple locations. The cutouts 170 may allow sections of the proximal lip to bend away from the adjacent section to facilitate insertion and/or removal.

Depending on the configuration of the adjacent section 172, the cutouts 170 may be positioned within (FIG. 18) the inner cannula connector 28 when the inner cannula is properly inserted or outside (FIG. 19) the inner cannula connector 28. For example, the adjacent section 172 may include a feature (e.g., a groove 190) that engages with a complementary feature near the proximal end 44 of the inner cannula connector 28. Depending in the configuration, the adjacent section 172 may be about 4 mm from the proximal end 34. In such an embodiment, the proximal lip is spaced apart from the proximal end 44 when the inner cannula 30 is inserted. The cutouts 170 provide a recess for improved engagement with the proximal lip.

Figure 20:
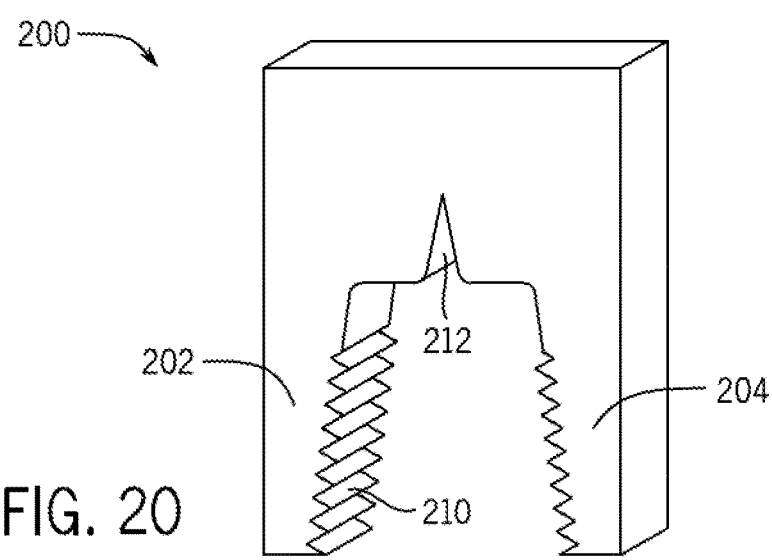
FIG. 20 is a perspective view of an insertion or removal device.
Figure 21:
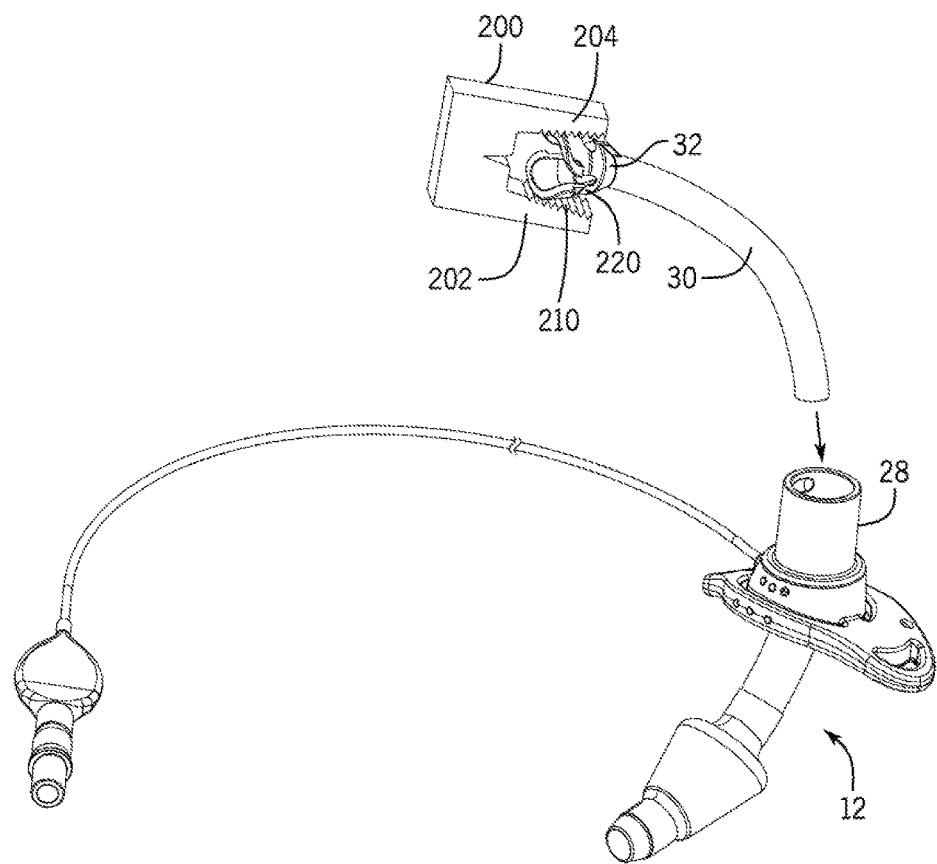
FIG. 21 is a view of the insertion or removal device of FIG. 20 engaged with an inner cannula.
Figure 22:
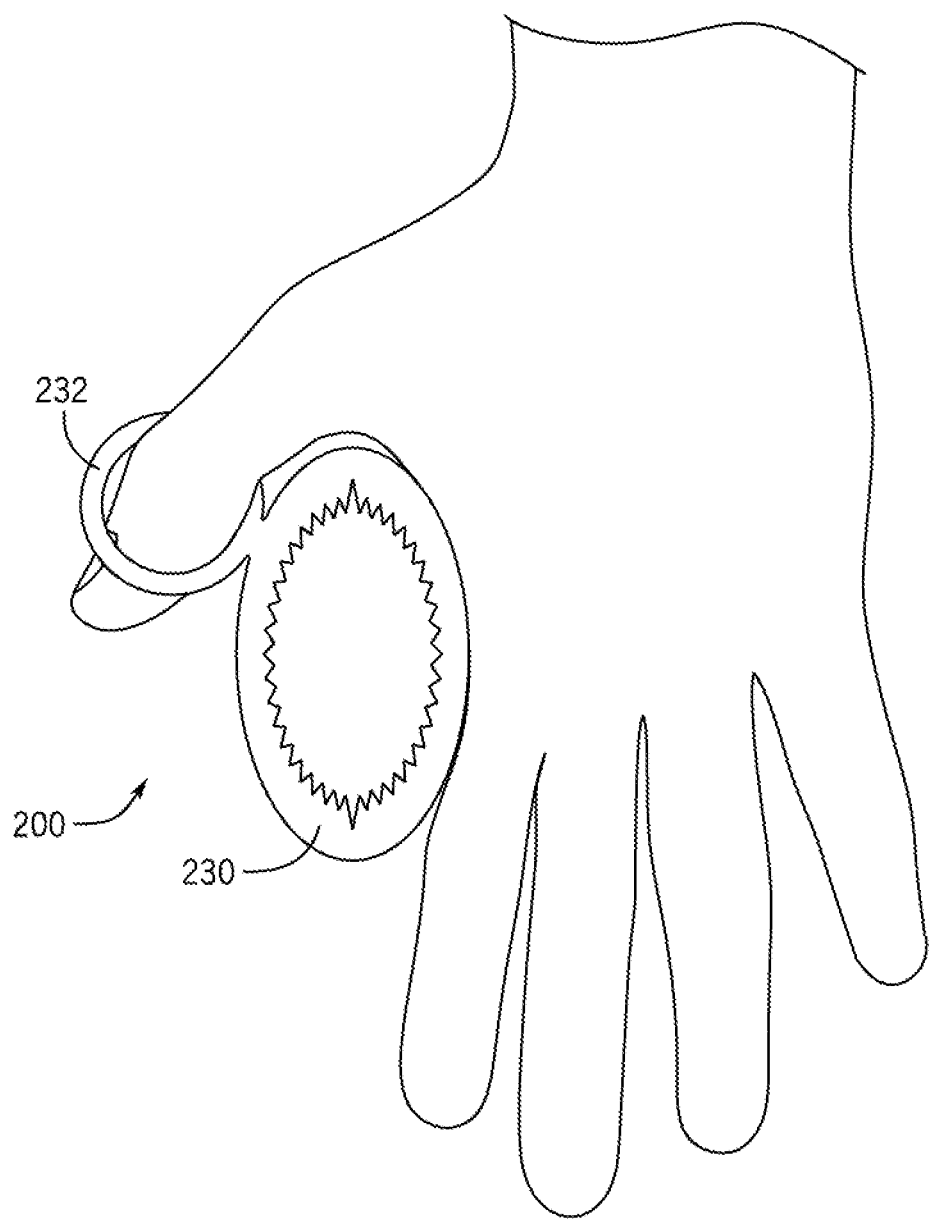
FIG. 22 is a view of an alternative annular insertion or removal device.
Figure 23:
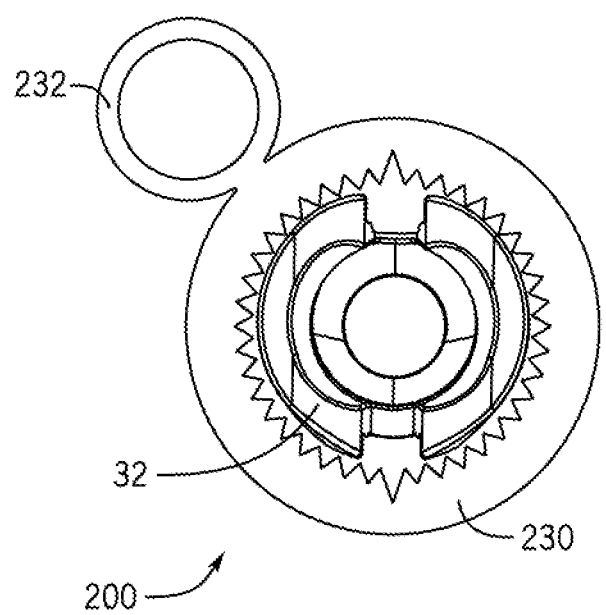
FIG. 23 is a view of the insertion or removal device of FIG. 22 engaged with an inner cannula.

In additional to features such as pull rings, the present techniques may include tools for facilitating inner cannula 30 removal and/or insertion. FIG. 20 shows an example of an insertion and/or removal device 200. The device may include a first member 202 and a second member 204 configured to engage opposing sides of a proximal end region of an inner cannula. The device 200 may also include engagement features such as gripping teeth 210 or a series of grooves and ridges configured to mate with complementary features on the inner cannula proximal end. To permit biasing of the first member 202 and the second member 204 toward one another, the device 200 may include a slit 212 that contracts when a biasing force is applied. FIG. 21 shows the device 200 engaged with the inner cannula 30, for example via gripping surface features 220 on the proximal end region 32 engaged with the gripping teeth 210. The device 200 may be used to insert or remove the inner cannula 30 from the outer cannula 12 and the outer cannula connector 28. FIG. 22 shows an alternate device 200 in the form of a compressible annulus 230 that may be grasped and, optionally, supported via a thumb or finger hold 232. FIG. 23 is a top view of the device 200 engaged with the proximal end region 32. The device 20 may be formed from a material resilient enough to compress the proximal end region under a biasing force applied by an operator, e.g., a plastic or metal. The device 200 may also include a shape memory material.

It is envisioned that the tracheal tube assembly 10, which may include the insertion and/or removal device 200 as provided herein, may be provided as an assembly and/or as a kit. A kit may include a packaging that encloses an inner cannula 30 sized for an outer cannula 12, which may include an affixed outer cannula connector 28 and flange member 20. The kit may also include a neck strap for retaining the tracheal tube 10 in place. The kit may also include an obturator. Other components of the kit may include a cap configured to be placed on a proximal end 34 while the obturator is in use and that may be part of the obturator. The tube assembly 10 components (e.g., outer cannula 12, flange member 20, outer cannula connector 28, cuff 16, and pilot balloon assembly 18) may be assembled prior to in situ assembly of the inner cannula 12 into the outer cannula 14. Indeed, the user or clinician may perform final assembly of the tracheal tube 10 by selecting a desired inner cannula 30 from a selection of inner cannulas and then inserting the inner cannula 30 into the outer cannula 12 prior to intubation, either by hand or with an insertion device 200. Thus assembled, the tracheal tube 10 may then be inserted into the patient's trachea.

It should be understood that any of the disclosed embodiments may be combined or exchanged with one another. By way of example only, it is envisioned that the inner cannula 30 may have one or more of the disclosed latches, windows, openings, proximal lips, cutouts, support ribs, pull rings, etc.

Components of the tube assembly 10 may be manufactured according to suitable techniques. For example, the inner cannula and/or outer cannula 12, including the outer cannula connector 28, may be molded, overmolded, two shot molded, computer numerical control (CNC) machined, milled, or otherwise formed into the desired shape. In one embodiment, a mold or mold form may be used to manufacture the inner cannula 30. In one embodiment, the mold or other manufacturing technique may facilitate a speckled outer surface of the inner cannula 30, which may facilitate insertion. One or more components may be manufactured of materials such as a polyethylene (e.g., low density polyethylene), polypropylene, PTFE, expandable PTFE, polyvinyl chloride (PVC), a PEBAX silicone, a polyurethane, thermoplastic elastomers, a polycarbonate plastic, a silicon, or an acrylonitrile butadiene styrene (ABS). In particular embodiments, the material of the inner cannula 30 may be selected to be 60 Shore D.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to airway devices, but these techniques may also be utilized for connections between inner and outer conduits for other types of medical devices and medical connective tubing. Rather, the various embodiments may cover all modifications, equivalents, and alternatives falling within the spirit and scope of the disclosure as defined by the following appended claims.

What is claimed is:

1. A tracheal tube assembly comprising:
an outer cannula configured to be positioned in a patient airway;
a flange member secured about the outer cannula;
an outer cannula connector coupled to a proximal end of the outer cannula;
an inner cannula configured to be disposed inside the outer cannula such that the inner cannula and the outer cannula are coaxial, wherein the inner cannula comprises a compressible proximal region that is configured to be positioned at least in part in the outer cannula connector and wherein the compressible proximal region of the inner cannula comprises a lip configured to be outside of the outer cannula connector when the inner cannula is fully inserted in the outer cannula, wherein the lip is a broken annulus separated by one or more opening or slits in a wall of the compressible proximal region of the inner cannula.

2. The assembly of claim 1, wherein the openings or slits narrow distally and interrupt the lip such that the lip is a broken annulus.

3. The assembly of claim 2, wherein the openings or slits are positioned on opposing sides of the compressible proximal region of the inner cannula such that the compressible proximal region of the inner cannula forms two opposing wings.

4. The assembly of claim 3, comprising a window in each of the two opposing wings.

5. The assembly of claim 3, wherein the compressible proximal region comprises only one opening or slit, and wherein the opening or slit terminates adjacent to a tapered portion of the inner cannula that narrows towards a distal end.

6. The assembly of claim 1, wherein the compressible proximal region comprises a plurality of openings partially separating the lip from an adjacent portion of the proximal end region.

7. The assembly of claim 6, wherein the lip is joined to the adjacent portion by one more ribs.

8. The assembly of claim 6, wherein the lip is configured to be a pull ring to facilitate removal of the inner cannula from the outer cannula and wherein the lip is configured to bend partially away from the adjacent portion when the inner cannula experiences a removal force.

9. The assembly of claim 1, wherein the compressible proximal region comprises a plurality of protrusions spaced apart from one another and positioned distally from the lip.

10. The assembly of claim 9, wherein the plurality of protrusions are different sizes.

11. The assembly of claim 1, wherein the compressible proximal region comprises a corrugated region configured to expand in length under an inner cannula removal force to facilitate movement of the lip away from the outer cannula connector.

12. A tracheal tube system comprising:
an outer cannula configured to be positioned in a patient airway;
an inner cannula configured to be disposed inside the outer cannula such that the inner cannula and the outer cannula are coaxial, wherein the inner cannula comprises a compressible proximal region that is configured to be positioned inside the outer cannula connector and wherein the compressible proximal region has a compressed configuration comprising a first diameter when positioned in the outer cannula connector and an uncompressed configuration comprising a second diameter when the compressible proximal region is unbiased and outside of the outer cannula connector; and
an insertion or removal device configured to press against an exterior of the proximal region to bias the proximal region into the compressed configuration, wherein the insertion device comprises an opening configured to accommodate the proximal region in the uncompressed configuration.

13. The tracheal tube system of claim 12, wherein a tip of the proximal region extends out of the outer cannula when the inner cannula is fully inserted in the outer cannula and wherein the insertion or removal device is configured to directly contact the tip to compress the proximal region.

14. The tracheal tube system of claim 12, wherein the opening comprises mating features configured to engage complementary features on the exterior of the proximal region.

15. The tracheal tube system of claim 14, wherein the mating features comprise grooves or teeth.

16. The tracheal tube system of claim 12, wherein the insertion or removal device comprises a compressible annulus configured to compress about the proximal region.

17. The tracheal tube system of claim 12, wherein the insertion or removal device comprises a first member and a second member configured to move towards one another to compress the proximal region.

18. The tracheal tube system of claim 12, wherein the system is assembled in a kit.

19. The tracheal tube system of claim 12, wherein the insertion or removal device is configured to engage a pull ring on the inner cannula.

* * * * *